(12) United States Patent (10) Patent No.: US 7,678,049 B2
Tsoref et al. (45) Date of Patent: Mar. 16, 2010

(54) BONE AGE ASSESSMENT USING ULTRASOUND

(75) Inventors: Liat Tsoref, Tel-Aviv (IL); Dov Furman, Rehovot (IL)

(73) Assignee: Beam-Med Ltd., Petach-Tikva (IL)

( * ) Notice: Subject to any disclaimer, the term of this patent is extended or adjusted under 35 U.S.C. 154(b) by 739 days.

(21) Appl. No.: 10/042,735

(22) Filed: Oct. 25, 2001

(65) Prior Publication Data

US 2003/0065264 A1 Apr. 3, 2003

Related U.S. Application Data

(63) Continuation of application No. PCT/IL01/00683, filed on Jul. 24, 2001.

(51) Int. Cl.
*A61B 8/00* (2006.01)
*A61B 8/02* (2006.01)
*A61B 8/06* (2006.01)
*A61B 8/12* (2006.01)
*A61B 8/14* (2006.01)

(52) U.S. Cl. ...... 600/437; 600/438; 600/442; 600/443; 600/448; 600/449; 600/459

(58) Field of Classification Search ......... 600/437–438, 600/442, 443, 448, 449, 459, 454, 450; 73/547, 73/549, 602
See application file for complete search history.

(56) References Cited

U.S. PATENT DOCUMENTS 4,490,640 A 12/1984 Honda
4,752,918 A 6/1988 Boucher et al.

(Continued)

FOREIGN PATENT DOCUMENTS

DE 3925014 1/1991

(Continued)

OTHER PUBLICATIONS

Kakuta et al., "Evaluation of Very Early Age Concrete Using a Wave Propagation Method," 1991, Taylor and Francis, p. 163 (Abstract) (From book entitled, "Quality Control of Concrete Structures").*

(Continued)

*Primary Examiner*—Brian Casler
*Assistant Examiner*—James Kish
(74) *Attorney, Agent, or Firm*—Martin Fleit; Paul D. Bianco; Fleit Gibbons Gutman Bongini & Bianco PL (57) ABSTRACT

A method and an apparatus for estimating bone age by at least one acoustic signal in an ossification-actuated skeletal structure. The apparatus includes an acoustic transmitter and an acoustic receiver positioned facing each other so that the structure is positioned between them. The structure has at least two bones. The transmitter is adapted for transmitting a signal to cross the structure transversely. An electronic moveable gantry is provided for adjusting the position of the acoustic transmitter and the acoustic receiver in relation to the structure. A computer system is enabled to perform one or more functions to position the moveable gantry; transmit the signal by the transmitter; control the signal transmitted by the transmitter; receive the transmitted signal by the receiver; and estimate bone age responsive to the received signal by at least one bone age calculation formula.

45 Claims, 4 Drawing Sheets

U.S. PATENT DOCUMENTS

| | | | |
|---|---|---|---|
| 4,774,959 A | 10/1988 | Palmer et al. | |
| 4,870,972 A | 10/1989 | Maerfeld et al. | |
| 4,913,157 A | 4/1990 | Pratt, Jr. et al. | |
| 4,926,870 A * | 5/1990 | Brandenburger | 600/437 |
| 4,963,782 A | 10/1990 | Bui et al. | |
| 5,197,475 A * | 3/1993 | Antich et al. | 600/437 |
| 5,452,722 A | 9/1995 | Langton | |
| 5,458,130 A * | 10/1995 | Kaufman et al. | 600/449 |
| 5,483,965 A * | 1/1996 | Wiener et al. | 600/449 |
| 5,487,388 A | 1/1996 | Rello et al. | |
| 5,509,042 A | 4/1996 | Mazess | |
| 5,532,169 A | 7/1996 | Eyre | |
| 5,533,519 A | 7/1996 | Radke et al. | |
| 5,564,423 A | 10/1996 | Mele et al. | |
| 5,577,089 A | 11/1996 | Mazess | |
| 5,605,155 A | 2/1997 | Chalana et al. | |
| 5,605,156 A | 2/1997 | Drzewiecki et al. | |
| 5,615,681 A | 4/1997 | Ohtomo | |
| 5,651,363 A * | 7/1997 | Kaugfman et al. | 600/438 |
| 5,704,356 A | 1/1998 | Shmueli | |
| 5,761,156 A | 6/1998 | Reuter et al. | |
| 5,806,520 A * | 9/1998 | Berger et al. | 600/442 |
| 5,824,085 A | 10/1998 | Sahay et al. | |
| 5,895,364 A * | 4/1999 | Donskoy | 600/595 |
| 6,035,227 A | 3/2000 | Shmueli | |
| 6,074,352 A | 6/2000 | Hynynen et al. | |
| 6,086,538 A | 7/2000 | Jørgensen et al. | |
| 6,095,979 A | 8/2000 | Ohtomo | |
| 6,135,960 A | 10/2000 | Holmberg | |
| 6,160,866 A | 12/2000 | Mazess et al. | |
| 6,244,101 B1 | 6/2001 | Autrey et al. | |
| 6,280,402 B1 | 8/2001 | Ishibashi et al. | |
| 6,306,089 B1 * | 10/2001 | Coleman et al. | 600/437 |
| 6,344,024 B1 | 2/2002 | Brucher et al. | |
| 6,413,215 B1 | 7/2002 | Wu et al. | |
| 6,454,712 B1 * | 9/2002 | Oonuki | 600/437 |
| 6,463,167 B1 | 10/2002 | Feldman et al. | |
| 6,468,215 B1 * | 10/2002 | Sarvazyan et al. | 600/438 |
| 6,585,666 B2 | 7/2003 | Suh et al. | |
| 6,607,487 B2 | 8/2003 | Chang et al. | |
| 6,799,066 B2 | 9/2004 | Steines et al. | |
| 6,836,557 B2 | 12/2004 | Tamez-Peña et al. | |
| 7,204,807 B2 | 4/2007 | Tsoref | |
| 2002/0162031 A1 * | 10/2002 | Levin et al. | 713/202 |
| 2003/0035773 A1 | 2/2003 | Totterman et al. | |
| 2003/0055502 A1 | 3/2003 | Lang et al. | |
| 2003/0229299 A1 | 12/2003 | Shimura et al. | |
| 2004/0193048 A1 | 9/2004 | Tsoref | |

FOREIGN PATENT DOCUMENTS

| | | |
|---|---|---|
| EP | 0341969 | 11/1989 |
| EP | 0 626 656 | 11/1994 |
| EP | 0 797 952 | 10/1997 |
| FR | 2 768 322 | 3/1999 |
| GB | 2257253 | 1/1993 |
| GB | 2321704 | 8/1998 |
| JP | 60-098799 | 6/1985 |
| JP | 07-303643 | 11/1995 |
| JP | 10-137239 | 5/1998 |
| WO | WO 00/28316 | 5/2000 |
| WO | WO 00/28361 | 5/2000 |
| WO | WO 00/62676 | 10/2000 |

OTHER PUBLICATIONS

Castriota-Scanderbeg, A. et al.; "Skeletal Age Assessment in Children and Young Adults: Comparison Between a Newly Developed Sonographic Method and Conventional Methods;" 1998; pp. 271-277; Skeletal Radiol; vol. 27.

Mughal, M. Z., et al.; "Assessment of Bone Status in Children Using Quantitative Ultrasound Techniques;" 1999; pp. 309-323; Chapter 17; Quantitative Ultrasound: Assessment of Osteoporosis and Bone Status; Edited by NJEH, C. F. et al.

Roche, A. F. et al.; "The RWT Method for the Prediction of Adult Stature;" Dec. 6, 1975; pp. 1026-1033; Pediatrics; vol. 56; No. 6.

Tanner, J. M. et al.; "Prediction of Adult Height from Height and Bone Age in Childhood;" 1983; pp. 767-776; Archives of Disease in Childhood; vol. 58.

Tanner, J. M. et al.; "Prediction of Adult Height from Height, Bone Age, and Occurrence of Menarche, at Ages 4 to 16 with Allowance for Midparent Height;" 1975; pp. 14-26; Archives of Disease in Childhood; vol. 50.

Lequin, M. H. et al.; "Normal Values for Tibial Quantitative Ultrasonometry in Caucasian Children and Adolescents (Aged 6 to 19Years);" 2000; pp. 101-105; Calcified Tissue International; vol. 67.

Sun, Y. N. et al.; "A ComputerSystem for Skeletal Growth Measurement;"Computers and BiomedicalResearch; vol. 27; 1994; pp. 2-12; XP002067754.

Wear, K. A. et al; "Assessment of Bone Density Using Ultrasonic Backscatter;"Jun. 1998; pp. 689-695; Ultrasound in Med Biol; vol. 24; No. 5.

Todd, T. W.; "Age Changes in the Pubic Bone;" pp. 285-334; American Journal of Physical Anthropology;vol. 3.; No. 3; Jul.-Sep. 1920.

Todd, T. W. et al.; "EndocranialSutureClosure, its Progress and Age Relationship;" American Journal of Physical Anthropology;vol. 7; pp. 325-384; 1924.

International Search Report Dated Jul. 1, 2002 From the International Searching Authority Re.: Application No. PCT/IL01/00763.

International Search Report Dated Mar. 1, 2002 From the International Searching Authority Re.: Application No. PCT/IL01/00683.

International Search Report Dated Apr. 15, 2003 From the International Searching Authority Re.: Application No. PCT/IL02/00612.

Notice of Allowance Dated Jun. 30, 2006 From the US Patent and Trademark Office Re.: U.S. Appl. No. 10/484,403.

Official Action Dated Aug. 3, 2006 From the US Patent and Trademark Office Re.: U.S. Appl. No. 10/484,399.

Official Action Dated Nov. 14, 2005 From the US Patent and Trademark Office Re.: U.S. Appl. No. 10/484,403.

Adler et al. "Quantitative Assessment of Cartilage Surface Roughness in Osteoarthritis Using High Frequency Ultrsound", Ultrasound in Medicine and Biology, XP008004715, 18(1): 51-58, 1992.

Aisen et al. "Sonographic Evaluation of the Cartilage of the Knee", Radiology, 153(3): 781-784, Dec. 1983.

Gahunia et al. "Osteoarthritis Staging: Comparison Between Magnetic Resonance Imaging, Gross Pathology and Histopathology in the Rhesus Macaque", Osteoarthritis and Cartilage, 3: 169-180, 1995.

Gonzalez et al. "Representation and Description", Digital Image Processing, Addison-Wesley Publishing Company, p. 506-518, 1992.

Grassi et al. "Sonographic Imaging of Normal and Osteoarthritis Cartilage", Seminars in Arthritis and Rheumatism, 28(6): 388-403, Jun. 1999. Abstract.

Haralick et al. "Textural Features for Image Classification", IEEE Transactions on Systems, Man, and Cybernetics, SMC-3(6): 610-621, Nov. 1973.

Iagnocco et al. "Sonographic Evaluation of Femoral Condylar Cartilage in Osteoarthritis and Rheumatoid Arthritis", Scandinavian Journal of Rheumatology, 21: 201-203, 1992. Abstract.

Jain "Image Filtering and Restoration/ Image Analysis and Computer Vision", Fundamentals of Digital Image Processing, Chap.8/9: 313-331/394-400, 1989.

Lefebre et al. "Automatic Three-Dimensional Reconstruction and Characterization of Articular Cartilage From High-Resolution Ultrasound Acquisitions", Ultrasound in Medicine and Biology, XP004295291, 24(9): 1369-1381, Dec. 1998.

McCune et al. "Sonographic Evaluation of Osteoarthritic Femoral Condylar Cartilage", Clinical Orthopaedics and Related Research, 254: 230-235, May 1990. Abstract.

Tomlinson et al. "Ultrasonographic Evaluation of Tarsocrural Joint Cartilage in Normal Adult Horses", Veterinary Radiology and Ultrasound, 41(5): 457-460, 2000. Abstract.

Van den Hoogen et al. "Effect of Exercise on the Proteoglycan Metabolism of Articular Cartilage in Growing Foals", Equine Veterinary Journal Supplement, 31: 62-66, 1999. Abstract.

Vince et al. "Comparison of Texture Analysis Methods for the Characterization of Coronary Plaques in Intravascular Ultrasound Images", Computerized Medical Imaging and Graphics, 24: 221-229, 2000.

Wilson et al. "Development of Automated Ultrasonic Measurements of Articular Cartilage Thickness and Surface Morphology", Biomechanics, Rehabilitation, Electrical Phenomena, Biomaterials, Proceedings of the Annual International Conference of the Engineering in Medicine and Biology Socitey, IEEE, New York, XP000452803, 3(Conf.15): 1122-1123, Oct. 28, 1993.

* cited by examiner

BONE AGE ASSESSMENT USING ULTRASOUND

RELATED APPLICATION

This application is a continuation of PCT Application PCT/IL01/00683, filed Jul. 24, 2001, which designates the United States.

FIELD OF THE INVENTION

The present invention relates to assessing bone age using ultrasound.

BACKGROUND OF INVENTION

Bone age assessment in growing subjects is a well-known diagnostic tool that is especially useful in predicting stature and/or growth problems in children, teenagers and adults. Many methods of assessing bone age are based upon radiographic analysis, such as the Greulich and Pyle (GP) method (Greulich W W, Pyle S I, Radiographic atlas of skeletal development of the hand and wrist, $2^{nd}$ ed. Stanford Calif., Stanford University Press, 1959.) and the Tanner and Whitehouse (TW2) method [Tanner, J M, Whitehouse, R H, Marshall, W A, et al. "Assessment of skeletal maturity and prediction of adult height" (TW2 method). NY, Academic Press], both of which assess bone age by the radiographic presentation of the bones of the wrist and hand. In the Greulich and Pyle method a comparison is made between the child's radiograph and the corresponding standard in the Greulich and Pyle atlas. In the TW2 method 20 bones in hand and wrist are scored according to their stage, thus producing a total score for which a skeletal age may be read directly from the tables.

These methods present problems of accessibility as X-ray units are often available only in secondary care centers such as hospitals. Additionally, ionizing radiation is undesirable in elective procedures, especially to children.

Allessandro Castriota-Scanderbeg et al., in "Skeletal age assessment in children and young adults: Comparison between a newly developed sonographic method and conventional methods," Skeletal Radiology 1998 27:271-277, propose a method for assessing skeletal age using ultrasound imaging measurements of the thickness of femoral head articular cartilage. In this method, a non-cartilage structure in an ultrasound image, an epiphysis, is linearly measured along a cross sectional plane without regard to structural aspects such as bone density. Further, this method is inaccurate and likely requires an imaging specialist for its administration, detracting from its cost-effectiveness.

Chalana et al. U.S. Pat. No. 5,605,155 uses ultrasound images for the measurement of fetal head structure to predict fetal head size. Hechard Patrick, FR 2768322 uses X-rays or ultrasound to measure the thickness of the epiphysis and metaphysis of a bone to establish an index used for assessing a "Ratio of Residual Growth." Holmberg, U.S. Pat. No. 6,135,960 proposes using ultrasound transducers placed in a Cartesian coordinate system for characterizing objects within the body. The above publications assess object boundaries utilizing dimensional ultrasound imaging techniques without regard to structural aspects such as bone density.

Ultrasonic methods of bone density measurement are known. For instance, according to prior art ultrasound measurement systems, (for example, WO 00/28316 and U.S. Pat. No. 5,564,423, the disclosure of which are incorporated herein by reference), ultrasound is used to determine the density of a non-cartilage osseous structure.

Thus use of backscatter attenuation to determine bone density is described by Wear, K A and Garra, B S, "Assessment of bone density using ultrasonic backscatter", *Ultrasound Med Biol,* 1998 June; 24(5):689-95.

Langton, et al. in "Quantitative Ultrasound" Chapter 17, p. 311-312, measure bone's speed of sound and broadband ultrasound attenuation in children using the center of the posterior portion of the Calcaneal, specifically so the ultrasound signal does not pass through the Calcaneal growth plate. This measurement area begins ossification prenatally so that this method estimates bone's speed of sound and broadband ultrasound attenuation based upon non-cartilage properties.

SUMMARY OF THE INVENTION

An aspect of some embodiments of the invention relates to estimating bone age from acoustic signals of ossifying structures.

In an exemplary embodiment of the present invention, bone age is estimated by measuring an acoustic velocity in cartilage structures that are in the process of ossifying wherein the velocity is expected to increase as a function of the ossification during the human maturation process. Such acoustic signal velocity, for example, is measured in primary ossification centers such as the bones of the wrist or secondary ossification centers such as the distal regions of the ulna and radius.

Optionally, two or more acoustic signals of one or more ossification centers are measured to determine bone age. Additionally or alternatively, the ratio of acoustic signals between two or more ossification centers is used to measure bone age. Additionally or alternatively, acoustic signals from structures associated with ossifying structures are used to measure bone age, for example, the fibrocartilage of the pubic symphysis, skull suture ligaments and tooth and mandibular changes.

Bone age may be used to predict adult stature or other aspects of the maturation process. Such predictions are based on bone age derived by other methods known in the art. Alternatively or additionally, tracking of ossification in bone is used to detect and/or track the progress of various disease states and/or disorders, with, for instance, a more accurate profile than X-ray evaluation due to its non-ionizing nature, allowing frequent monitoring without harm.

In an exemplary embodiment, parameters other than acoustic velocity, such as broadband ultrasound attenuation (BUA) and dispersion of ultrasound signal, are used to estimate bone age, for example by correlating these parameters with the known BA assessment of a group of children. Additionally or alternatively, signals reflected from bone are used to measure bone age, for example, by measuring attenuation of backscatter intensity of the ultrasound signal.

Optionally, especially for some types of measures and/or where object boundaries are unclear, a scanning or multi-beam measurement system may be used. Optionally, the acoustic signal provides a spatial measure, for example, indicating a profile of velocity along a bone axis or a radial profile of an ossification center.

Different bones, different measures and/or different measurement systems may be used for different situations and/or for analyzing different bone ages or disease states.

An aspect of some embodiments of the invention relates to using an existing osteoporosis measurement device, possibly with minimal changes, to assess bone age. In one example, a device designed for measuring osteoporosis in a finger is reprogrammed with a table that associates acoustic velocities with bone ages, rather than with states of osteoporosis.

Further, the transducers for measuring acoustic signal are modified specifically for application to growth centers. It is noted that velocity limits used in osteoporosis measurement-devices are designed to obtain measurements from non-growth center areas.

There is thus provided, in accordance with an exemplary embodiment of the invention a method for measuring bone age comprising:

transmitting an acoustic energy into the body of a subject;

receiving an acoustic signal from one or more structures including an ossification-actuated skeletal structure or a cranial structure that changes with age, responsive to said transmitted acoustic energy;

analyzing the acoustic signal to determine at least one effect of said structure on said signal; and estimating the age of the structure from said determined effect.

Optionally, said ossification-actuated skeletal structure comprises one or more areas undergoing ossification. Optionally, said ossification-actuated skeletal structure comprises one or more bones. Optionally, said ossification-actuated skeletal structure comprises one or more regions of cartilage. Optionally, said ossification-actuated skeletal structure comprises one or more regions of non-cartilage soft tissue. Optionally, said ossification-actuated skeletal structure comprises one or more regions of fibrocartilage.

In an embodiment of the invention, said ossification-actuated skeletal structure comprises a region with one or more primary ossification centers. Optionally, said ossification-actuated skeletal structure comprises one or more of: the bones of the wrist, the bones of the palm, the bones of the tarsus, the mandible.

In an embodiment of the invention, said ossification-actuated skeletal structure comprises a region with one or more secondary ossification centers. Optionally, said ossification-actuated skeletal structure contains an epiphysis. Optionally said ossification-actuated skeletal structure comprises a region of one or more of: an ulna, a radius, a femur, a bone of a ray of an extremity.

Optionally, said receiving comprises utilizing two or more different acoustic signals to provide a measure of bone age. Optionally, said two or more acoustic signals are associated with the same bone. Optionally, said two or more acoustic signals are associated with paths in different bones. Optionally, said two or more acoustic signals are received from the same direction. Optionally, said two or more acoustic signals are received from the different directions.

In an embodiment of the invention, said signal passes through said one or more structures including an ossification-actuated skeletal structure.

In an embodiment of the invention, said signal echoes from said one or more structures including an ossification-actuated skeletal structure.

Optionally, said analysis of said signal is responsive to speed of sound from said one or more structures including an ossification-actuated skeletal structure.

Optionally, said analysis of said signal is responsive to broadband ultrasound attenuation from said one or more structures including an ossification-actuated skeletal structure.

Optionally, said analysis of said signal is responsive to dispersion of ultrasound from said one or more structures including an ossification-actuated skeletal structure.

Optionally, said analysis of said signal is performed, at least in part, in the frequency domain. Optionally, said analysis of said signal is performed, at least in part, in the time domain.

In an embodiment of the invention, said analysis of said signal is responsive to attenuation of an ultrasound signal in said one or more structures including an ossification-actuated skeletal structure.

Optionally, said analysis is used to predict adult stature.

In an embodiment of the invention, to provide an estimate of bone age, said analysis is compared to a database having correlation with one or more of: conventional radiographs, CT images, MRI images and Nuclear Medicine scans.

In an embodiment of the invention, said transmitting is by a scanning acoustic signal transmitter.

In an embodiment of the invention, said transmitting is by a multi-beam acoustic signal transmitter.

Optionally, said receiving provides two or more acoustic signal measures along an axis of said one or more structures including an ossification-actuated skeletal structure.

Optionally, said receiving provides two or more acoustic signal measures radially around said one or more structures including an ossification-actuated skeletal structure.

In an embodiment of the invention, said analysis is correlated with a known bone age measurement system.

In an embodiment of the invention, said analysis is responsive to a formula providing a correlation with a known bone age measurement system. Optionally, is responsive to at least one of: speed of sound, broadband ultrasound attenuation, scattering and dispersion of acoustic signal through or from an ossification activated skeletal structure. Optionally, an estimate of bone age is responsive to time of flight of an acoustic signal between two transducers, with said ossification activated skeletal structure being situated intermediate to said transducers.

Optionally, separate formulas are used to correlate known bone age data with acoustic signals from males and females.

In an embodiment of the invention, said acoustic information is constructed into a database of bone age measurements. Optionally, said database is arranged according to one or more of: sex, ethnic group, geographic location, nutrition and general inheritance. Optionally, said database includes two or more measurements of one or more of said one or more structures including an ossification-actuated skeletal structure. Optionally, said database includes one or more measurements of two or more growth stages from said one or more structures including an ossification-actuated skeletal structure Optionally, said database includes one or more measurements of said one or more structures including an ossification-actuated skeletal structure in two or more populations.

Optionally, said received signals are compared to similar signals in a database to predict one or more of predict one or more of adult bone length, density, thickness and resilience and adult stature. Optionally, said received signals are compared to similar signals in a database to indicate a bone-growth related disorder. Optionally, said received signals are compared to similar signals in a database to track the progress of a bone-growth related disorder. Optionally, said received signals are compared to similar signals in a database to track hormone therapy in a growth stature disorder. Optionally, said received signals are compared to similar signals in a database to indicate one or more growth-plate related disease states, including osteogenic sarcoma, slipped growth plate, premature arrest of growth plate growth and inflammation of growth plate.

Optionally, two or more acoustic measurements are made on a single subject and entered into said database. Optionally, said two or more acoustic measurements are compared to track one or more growth-related disorders, including precocious puberty, delayed puberty, rickets, kwashiorkor, hypoparathyroidism, pituitary dwarfism and diabetes.

Optionally, said two or more acoustic measurements are compared to track treatment of one or more growth-related disorders, including precocious puberty, delayed puberty, rickets, kwashiorkor, hypoparathyroidism, pituitary dwarfism and diabetes.

There is further provided, in accordance with an exemplary embodiment of the invention, an apparatus for estimating bone age comprising:

an acoustic transmitter and an acoustic receiver positioned on either side of one or more structures including an ossification-actuated skeletal structure;

an electronic moveable gantry that adjusts the position of said acoustic transmitter and said acoustic receiver in relation to said ossification-actuated structure;

a computer system that performs one or more functions of:

positioning of said moveable gantry;

controlling acoustic signals transmitted by said acoustic transmitter;

receiving acoustic signals from said receiver responsive to said transmitted signals; and estimating said bone age responsive to said received signals.

In an embodiment of the invention, said apparatus transmits and receives one or more acoustic signals linearly along an axis through said ossification-actuated structure.

In an embodiment of the invention, said apparatus transmits and receives one or more acoustic signals radially around an axis through said ossification-actuated structure.

Optionally, said computer system controls said acoustic signal transmitter to provide an acoustic signal appropriate for said ossification-actuated structure.

Optionally, said computer system estimates said bone age responsive to one of more of broadband ultrasound attenuation, acoustic backscatter, dispersion of acoustic signal and speed of sound in said ossification-actuated structure.

Optionally, said computer system uses an imager to control the position of said acoustic signal receiver and said acoustic signal transmitter.

Optionally, said computer system contains a visual display to provide information on said bone age. Optionally, said visual display comprises a graph.

Optionally, said computer system is comprised in a computer network.

Optionally, said computer system comprises a neural network.

Optionally, said computer system compares said received acoustic signal to a database containing information of one or more acoustic signals from one or more structures including an ossification-actuated skeletal structure to provide an estimate of bone age.

Optionally, said computer system compares said received acoustic signal to a database containing information of one or more acoustic signals from one or more structures, including an ossification-actuated skeletal structure to predict stature. Optionally, said computer system compares said received acoustic signal to a database containing information of one or more acoustic signals from one or more structures including an ossification-actuated skeletal structure to indicate, track or follow treatment of one or more of: a bone-growth related disorder, a growth plate disorder, and a growth related disorder.

BRIEF DESCRIPTION OF THE DRAWINGS

Exemplary non-limiting embodiments of the present invention described in the following description, read with reference to the figures attached hereto. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are.

DETAILED DESCRIPTION OF EXEMPLARY EMBODIMENTS

Figure 1:
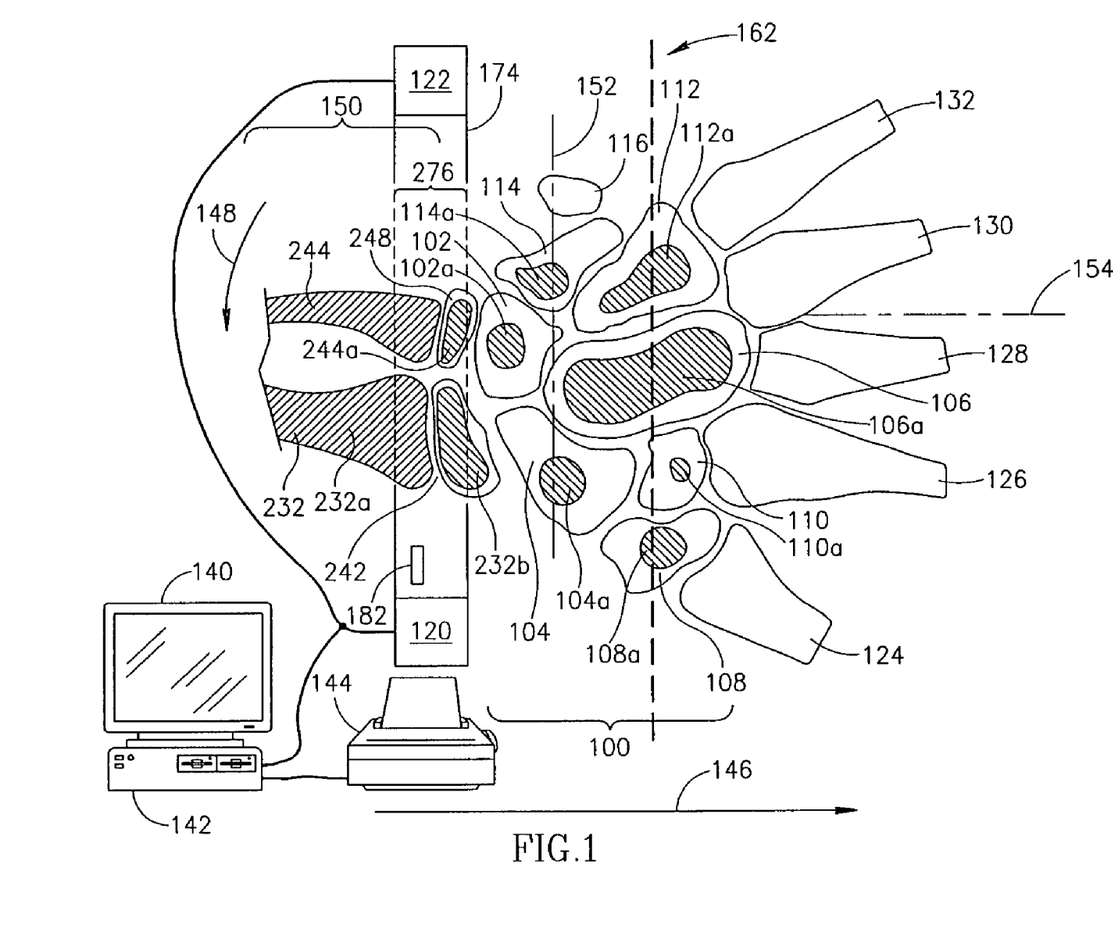
FIG. 1 schematically illustrates ultrasound measurements of ossifying wrist and arm bones of a 6.5-year-old male, in accordance with an embodiment of the present invention.

FIG. 1 illustrates ultrasound measurements of a portion of an arm 150 and a wrist 100 of a 6.5-year-old male in accordance with an exemplary embodiment of the present invention. Each bone of wrist 100 exhibits an ossification center, represented by a crosshatched area, that begins from a central portion and progresses toward the periphery and is referred to as a "primary ossification center". Bones with only primary ossification centers continue to show changes in acoustic velocity due to increased ossification, increased bone size and/or changes in bone shape through the 15th-19th years. Some bones have additional ossification centers that appear as a strip of cartilage between ossified bone sections, referred to as a "secondary ossification center."

A radius 232, for instance, contains a secondary ossification center consisting of a cartilaginous growth plate 242 that is situated between an epiphysis 232b and a metaphysis 232a, both of which are ossified. Growth plate 242 first appears in the first postnatal year and ossifies in the seventeenth year in females and in the nineteenth year in males. When a secondary ossification center ossifies, at a later age, epiphysis 232b and metaphysis 232a fuse together with growth plate 242 that ossifies as well. After the stage when fusion occurs, bone 232 is fully ossified lacking the bands of cartilage and hence is radio-opaque throughout.

Ulna 244 similarly contains a growth plate 244a that appears in the fifth year in females and in the sixth year in males. Ulnar growth plate 244a ossifies in the seventeenth year in females and eighteenth year in males.

In an exemplary embodiment, two transducers, such as a receiver 122 and a transmitter 120, are held in a gantry 174 and placed so that they are in contact with the skin over ulna 244 and radius 232. The thickness of soft tissue covering the bone is measured or the effect of soft tissue is optionally ignored. Transducers 122 and 120 are positioned so that they transmit along a region 276, to obtain acoustic signals from ulna 244 and radius 232 and their respective ossification centers. This method of ultrasound transmission is referred to herein as a "through" method. In an exemplary embodiment, the frequency of transducers 122 and 120 is between 300 kHz to 2 MHz. The distance between transducers 122 and 120 is measured using a ruler in which the distance is indicated by a digital readout 182.

Generally, the transducers are controlled and the received signals processed by a controller 142 (e.g., a computer), which optionally includes a display 140 and/or a printer 144.

The acoustic signal from a growth plate, such as ulna growth plate 244a, is markedly different than that of bone, such as bone 244. One parameter that can be measured from the obtained acoustic signal is the speed of sound. The distance between transducers is evaluated by digital ruler 182 that is connected to transducers 120 and 122 and the average speed of sound is calculated by dividing the distance between the transducers by the transmission time. Alternatively or additionally the distance between the transducers can be measured using optic or acoustic distance measurement devices. The speed of sound in ulnar cartilage 244a is about 1700 meters per second (m/s) while speed of sound in bone 244 is about 2000-4500 m/s, depending on probe localization and age. The transmission time of a signal varies based upon the composition of the structures in the path, which changes with age.

An ultrasound signal passing along region 276 will pass through ossified ulna 244, ulnar growth plate cartilage 244a, and ulnar epiphysis 248 that is also ossified. It continues through ossified radial epiphysis 232b, radial growth plate cartilage 242 and ossified radius 232.

The acoustic path in the measurement of speed of sound, for example, is based upon the time of flight of the first acoustic signal to arrive at the receiver. As bone provides the fastest acoustic signal transmission time, the first received ultrasound signal indicates the path with the greatest ossification in a given area. The first ultrasound signal passing through region 276, for example, will be markedly faster than the first ultrasound signal transmitted in an area along axis 152, due to the greater amount of ossification in area 276.

The acoustic signal from transducers 122 and 120, taken along region 276 is sent to a controlling unit 142, and can be analyzed either locally, such as using a PC, or remotely through a computer network. Such analysis can be immediate or the information can be stored and analyzed at a later time. Further, the analysis may be based upon, for instance, spectral analysis (frequency domain) and/or temporal analysis (time domain), which are known to characterize biological tissue.

Other parameters that can be obtained from the acoustic signal include, dispersion and Broadband Ultrasound Attenuation. Dispersion is the slope at which the speed of sound changes with frequency. Dispersion is calculated from the dispersion graph, which is the curve of speed of sound versus frequency, calculated using the phase of each Fourier component of the signal and the distance. In a linear graph, the dispersion value is the slope of the graph and is given in units of $m \cdot s^{-1} \cdot MHz^{-1}$.

Broadband ultrasound attenuation is the value of the slope at which attenuation changes with frequency. Broadband ultrasound attenuation is calculated from an attenuation graph, which is the curve of the logarithm of amplitude of the Ultrasound signal versus frequency, calculated using the amplitude of each Fourier component of the signal and the distance. If the attenuation graph is linear, the broadband ultrasound attenuation is the slope of the graph in units of $db \cdot cms^{-1} \cdot MHz^{-1}$.

In an exemplary embodiment of the invention, a database is established of children of different ages that contains the children's ultrasound parameters and their bone age as assessed by conventional radiograph. Statistical algorithms, for instance, can be used to correlate the ultrasound parameters and the bone age.

In an exemplary embodiment, such an algorithm correlates speed of sound measured from the radius-ulna site, including the metaphysis and epiphysis, to radiographic bone age of the wrist and palm as read by the Greulich and Pyle (see Greulich and Pyle reference noted above) whereby acoustic signals provide the Bone Age (BA) utilizing equations such as:

$$BA=(SOS-1566)/27.9 \text{ for females} \qquad [\text{Eq. 1}]$$

$$BA=(SOS-1655)/15.6 \text{ for males,} \qquad [\text{Eq. 2}]$$

Where speed of sound (SOS) is in units of m/s and bone age (BA) is given in years. These formulae, for instance, are valid for an age range of 4-18 years.

Multi Parameter Bone Age Assessment

In an exemplary embodiment of the invention two or more of the following parameters are obtained from the ultrasound signal are used to provide an estimation of bone age: The distance (D), in mm, between the transmitter and receiver probes, the time (T1) of the arrival of the pulse, calculated by extrapolating a linear fit, as explained below, to the zero-signal level and the time (T2) of receipt of the pulse front, calculated by interpolating the same linear fit as in T1 to the signal half-amplitude level.

The linear fit is calculated on several data points around the first half-amplitude level of the first half-wave of the ultrasound pulse. This type of processing requires that the first half wave of the ultrasound signal will not be saturated.

In an exemplary embodiment, all three parameters are formulated to calculate two new parameters. C1=D/T1 and C2=D/T2, and uses a linear combination of T1, T2, C1 and C2 as an estimator to the bone age:

$$BA=a1 \cdot C1+a2 \cdot C2+a3 \cdot T1+a4 \cdot T2+b, \qquad [\text{Eq. 3}]$$

Where a1, a2, a3, a4 and b are constants in the model. Optionally, this model uses different sets of constants for males and females.

Figure 4:
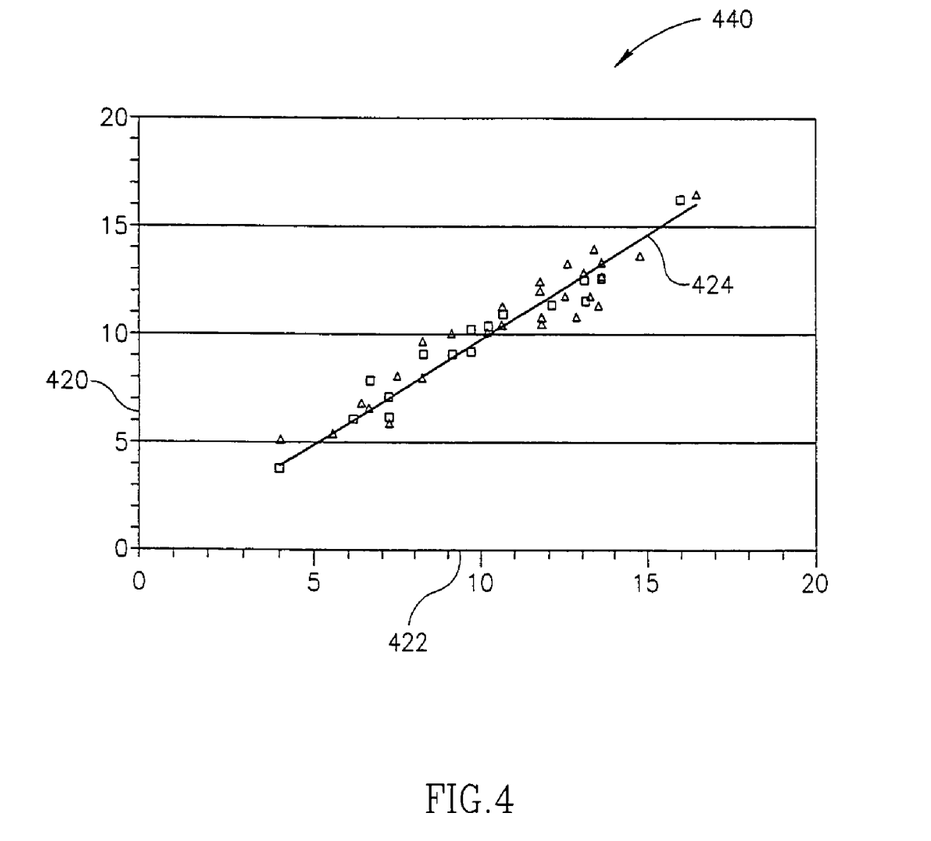
FIG. 4 is a graph of Bone Age of the hand assessed by ultrasonic multi parameter model as compared to standard X-ray.

For males: a1=0.35; a2=−0.32; a3=22.7; a4=−22.5; b=−56.8;

For females: a1=0.14; a2=−0.13; a3=10.1; a4=−9.8; b=−31.0;

FIG. 4 is an exemplary embodiment of a graph 410 of bone age of hand 200, assessed by ultrasonic multiparameter model as compared to standard X-ray for a population of girls represented by square marks and a population of boys, represented by triangular marks. A y axis 420 represents the bone age calculated by a multiparameter model on graph 440 and an x axis 422 represents the bone age calculated using X-ray on graph 440, with line 424 demonstrating the best linear fit to the results. Graph 410 demonstrates an $R^2$ obtained for this correlation of 0.92 where $R^2$ is the square of the Pearson Correlation Coefficient.

Bone Age Estimated From Other Sites

Wrist bones 100 comprise a Lunate 102, a Scaphoid 104, a Capitate 106, a Trapezium 108, a Trapezoid 110, a Hamate 112, a Triquetral 114 and a Pisiform 116.

Wrist bones 100 are cartilaginous at birth. Ossification, the process by which cartilage is replaced with bone, begins soon after birth in Capitate 106. Ossification centers appear in bones on a regular pattern and predictably increase in size until skeletal maturation in the late teens. At age 6.5, most of the bones of wrist 100 contain a region of ossification, represented by the shaded areas, while the clear areas represent regions that are still made up of cartilage. Ossified regions contain calcium that is relatively opaque to X-ray, whereas cartilage does not contain calcium and is not well differentiated over other soft tissue in the body on X-ray images. Thus the shaded areas would appear less dense on an X-ray image on a fairly uniform dense background.

The ossified areas of wrist 100 of a 6.5-year-old male are: the Lunate 102a, the Scaphoid 104a, the Capitate 106a, the Trapezium 108a, the Trapezoid 110a, the Hamate 112a and the Triquetral 114a. Pisiform 116 will not begin to ossify until the $9^{th}$ to $12^{th}$ year.

In an exemplary embodiment of the invention, velocity in wrist 100 is measured by transmitting an ultrasonic signal from transducer 120 to transducer 122 with the transducers 120 and 122 moved so that they transmit and receive along axis 152. In an exemplary embodiment of the invention, the distance between transducers 120 and 122 is fixed or known. For instance, the distance is measured by ruler 182 with a digital readout that is connected to ultrasound transducers 120 and 122 so that the average velocity through wrist 100 can be determined.

As indicated, the measured average velocity is assumed to be a function of the ratio between soft tissue (including cartilage) and ossified or partly ossified tissue. Therefore, the velocity of the acoustic signal is an indicator of bone age. By varying the location of measurement, a more exact estimate may be provided, for example, indicating which particular bones have ossified and which have not.

Alternatively or additionally, a statistic of the velocity may be used for bone age assessment, for example, maximal, average or minimal velocity or any percentile or the velocity along a certain line in wrist 100. In an exemplary embodiment these should be compared to the bone age A formula using one or more of these statistics, or a combination of these statistics is correlated with the bone age as assessed by standard age determination methods such as using the Greulich and Pyle method. Ultimately, the best correlative formula is utilized to provide a standard reference upon which bone age assessment is based.

The above-defined methods are in distinct contrast to those of Langton, et al. ("Quantitative Ultrasound" Chapter 17, p. 311-312) who use a portion of non-cartilage Calcaneus as a basis for measuring bone's speed of sound and broadband ultrasound attenuation as noted above. There is no mention of bone age measurement in this reference.

Assessing Bone Age Using Ultrasound Along a Defined Path

Using various methods, as described below, bone age can be measured in premature babies, from birth through infancy, childhood, puberty, and teenage years and beyond. For instance, in the second month following birth, Capitate 106 ossification center appears within area marked 106a and an acoustic signal traveling through Capitate 106 will travel faster than a signal transmitted immediately following birth when Capitate 106 and all wrist 100 bones are cartilaginous. Even prior to the second month when Capitate ossification center 106a appears, the density of parts of Capitate 106 may increase, indicating the amount of time that has passed since birth. Such increase may occur in other bones as well. Thus, by determining the acoustic velocity associated with ossification of infant wrist 100, bone age can be estimated.

Capitate ossification center 106a continues to increase in size. At the end of the third month, the ossification center of Hamate 112a appears and bone age can be measured based upon the amount of ossification in either bone or both bones simultaneously. Hamate 112 and Capitate 106 continue to ossify, so that when transducers 120 and 122 are put in a position so that the acoustic signal travels along dashed line 162, it has a higher velocity in the ninth month and a still higher velocity in the second year, providing a measure of bone age.

Such measurements soon after birth have application, for instance, in judging crucial maturation progress of premature babies who are born with fetal bone structure according to the month of gestation at which they were born. For example, a premature baby born after 4.5 months of gestation will not have bone ossification of Capitate 106a until the equivalent of 9 months gestation plus one month. By measuring premature baby bone age, appearance of ossification in Capitate 106a, signifies a real age of one-month though the baby is 5.5 months postpartum. Ultrasound, being non-ionizing as is a radiograph beam, is much more suited for making these measurements on pediatric subjects, particularly when multiple measurements are made.

With time, other bones develop ossification centers. For instance, Triquetral ossification center 114a appears in the third year, while Lunate ossification center 102a appears during the fourth year, providing increased ossification density and faster speed of sound for measuring bone age along paths that include these structures.

The ossification centers in the Scaphoid (104a), the trapezium (108a), and the trapezoid (110a), appear in the fourth year in females and the fifth year in males and continue to increase in size, providing further acceleration of acoustic signals for measuring bone age. Pisiform 116 ossification center 116a appears in the ninth or tenth year in females and the twelfth year in males and continues to increase in size, providing further acceleration of acoustic signals for measuring bone age.

Shown for reference only, without ossification, are the bases of metacarpals, associated with Thumb, 124, index finger 126, middle finger 128, ring finger 130 and pinkie finger 132.

In one embodiment of the invention, ultrasound transmitter 120 and ultrasound receiver 122 remain stationary during the transmission and reception of ultrasound signals that pass through two or more bones of wrist 100. Ultrasound transducers 120 and 122 are positioned in a specific relationship to wrist 100, such as with both transducers in contact with the skin over one of more bones. In the present set-up, for instance, ultrasound transmitter 120 is set in position near base of metacarpal 132, at Pisiform bone 116 and ultrasound receiver 122 is set in position near metacarpal 124, over Scaphoid bone 104. This position allows a signal to travel along axis 152, through non-ossified Pisiform 116, ossified 114a and non-ossified portions of Triquetral 114, Capitate non-ossified portion 106, and ossified portion 104a and non-ossified portions of Scaphoid 104. The amount of skin and muscle tissue over these structures is small, so the acoustic signal transmitted along axis 152 has a velocity that reflects the amount of ossification along its path.

Additionally or alternatively, measurement is made of a single wrist bone. For instance, ultrasound transmitter 120 is positioned on the dorsal surface of the hand, directly over Trapezoid 108. Ultrasound receiver 122 is positioned on the ventral surface of the hand directly below Trapezoid 108. The amount of ossification in the bone results in a specific acoustic velocity that provides a measure of bone age.

Ultrasound transmitter 120 and ultrasound receiver 122 can be positioned over a variety of individual wrist structures to measure age. For instance, in the second month, over the dorsal and ventral surfaces of Capitate 106 and in the third month over the dorsal and ventral surfaces of Hamate 112. In addition, both individual bones and multi-bone paths can be measured for determining a bone age single estimate using statistical analysis. The statistical analysis can be performed using discriminant analysis, binaric logistic regression, multinomial logistic regression or neural networks methods.

Alternatively, a ratio between the acoustic signal velocity of two ossifying bones (or paths) is used to measure bone age. For instance, at the end of the fourth month, one month after Hamate 112 begins ossification; ultrasound transducers 120 and 122 are positioned over the dorsal and ventral surfaces over Hamate 112 to provide one measure of acoustic velocity. Transducers 120 and 122 are then placed over the dorsal and ventral surfaces of Capitate 106 to provide a second measure of acoustic velocity. These two acoustic signal velocities provide a ratio as a measure of bone age. Alternatively, two or more sets of transducers are used.

In an exemplary embodiment transducers 120 and 122 are modified specifically for obtaining measurements from the wrist, with the transducer shape being, for instance, of a size and shape that matches the size and shape of wrist bones 100. Optionally, the gantry is designed to place the transducers against the skin automatically or manually. For instance one transducer remains fixed in position and the other transducer is moved in relation to the hand to place a standard pressure against the skin. Such a transducer may incorporate a calibrated pressure-sensitive sensor within the head to provide optimal accuracy of pressure. Optionally, the hand is held in a bed that can move up or down in relation to the position of transducers 120 and 122, so that a standard acoustic path is traced through wrist 100. An imager may be provided to better locate the path 276 of acoustic signal, either signaling the operator to make positional adjustments of wrist 100 in relation to transducers 120 and 122, or, optionally, making such adjustments automatically.

Optionally, measurement using ultrasound transducers 120 and 122 is repeated at a plurality of locations, for example, locations along a reference line 146 or in a radial fashion according to a reference 148. Such measurement provides spatial acoustic information of one or more of a plurality of ossification centers from one or more of a plurality of reception and transmission points. Such acoustic velocities provide an acoustic map of wrist 100 for measuring bone age. Additionally or alternatively, two or more such acoustic velocities can be used to provide a ratio as a measure of bone age. Additionally or alternatively, two or more such acoustic velocities are averaged to provide a measure of bone age.

In an exemplary embodiment of the invention, spatial information is provided as a profile of velocities. Such a profile may be used, for example, to locate an area of minimum or maximum velocity, to locate an ossified or partially ossified area and/or to detect and/or identify abnormal ossification patterns. Such a profile can be generated, for example, using a computer system that maintains a record of the coordinates of the probes along with acoustic signal measurements. This data is displayed by the computer system, for example, as a 3D graph with 2 spatial axes and one speed of sound axis. Additionally or alternatively, the data provides a basis for directives on the further placement, movement or changes in signal frequency or signal analysis from probes 122 and 120. In an exemplary embodiment, computer system 142 automatically controls gantry 174 and transducers 120 and 122.

Additionally or alternatively, a first acoustic velocity is measured along one axis such as along line 146 and a second acoustic velocity is measured along another axis such as along line 154 and these values are averaged or placed in a ratio to provide a measure of bone age.

Additionally or alternatively to moving transducers, transducer 120 and/or transducer 122 (e.g., receiver and/or transmitter) comprises an acoustic transmission grid that transmits multiple signals at specific time/space intervals. The multiple input and output points provide spatial measurements of the bone velocity and hence the extent and location of ossification and ossification centers. Alternatively or additionally, one or both of transducers 120 and 122 is a phased array beam scanning transducer.

Figure 2A:
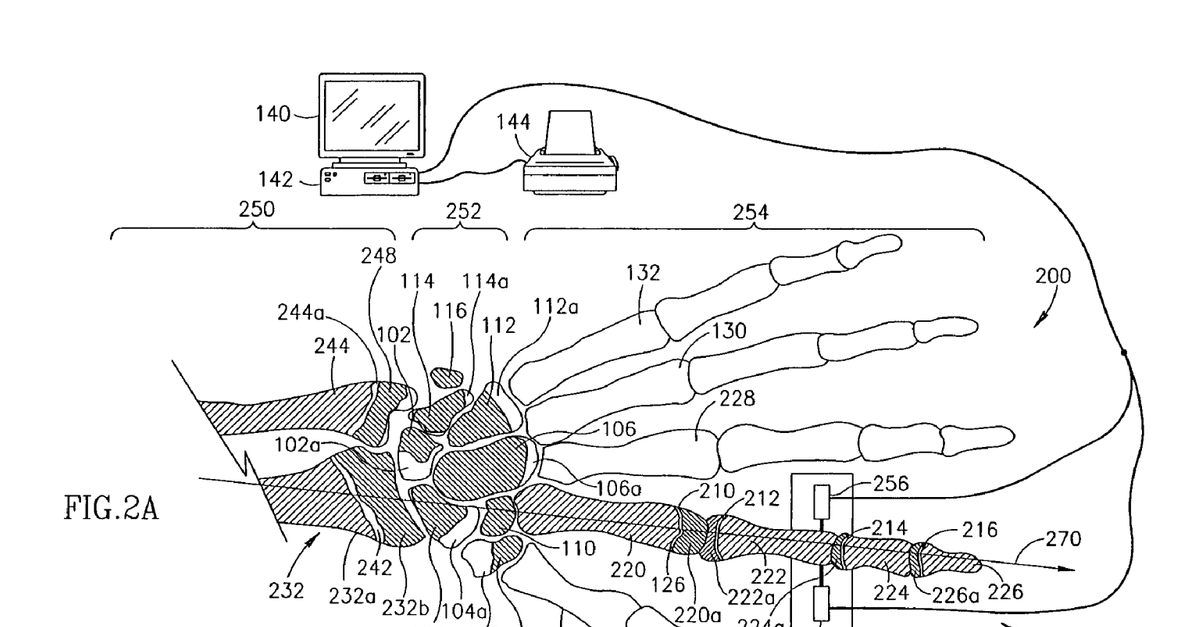
FIG. 2A schematically illustrates ultrasound measurements of a portion of ossifying arm, wrist and hand bones of an 11 year old female in accordance with an embodiment of the present invention.

FIG. 2A illustrates ultrasound measurements of a portion of an arm 250, a wrist 252 and digit structures 254 of an 11-year-old female in accordance with an exemplary embodiment of the present invention. The ossified portions of wrist 252, comprise a Scaphoid 104a, Capitate 106a, Trapezium 108a, Trapezoid 110a, Hamate 112a and Triquetral 114a, which show greater ossification than in 6.5 year-old male wrist 100 of FIG. 1. Additionally, Pisiform 116 has begun to ossify in region 116a. Corresponding to these changes, the acoustic signal from each of these bones will show increase in velocity over those of 6.5-year-old wrist 100 illustrated in FIG. 1.

Secondary growth plates are also seen in the bones of the rays of each digit. A ray 270, for instance, contains a distal phalanx 226 with a secondary growth plate 216 and epiphysis 226a; a middle phalanx 224 with a secondary growth plate 214 and an epiphysis 224a; a proximal phalanx 222 with a secondary growth plate 212 and epiphysis 222a; and a metacarpal 220 with a secondary growth plate 210 and epiphysis 220a. Shown for reference, without ossification patterns, are metacarpals and associated rays of thumb, 124, middle finger 128, ring finger 130 and pinkie finger 132.

Figure 2B:
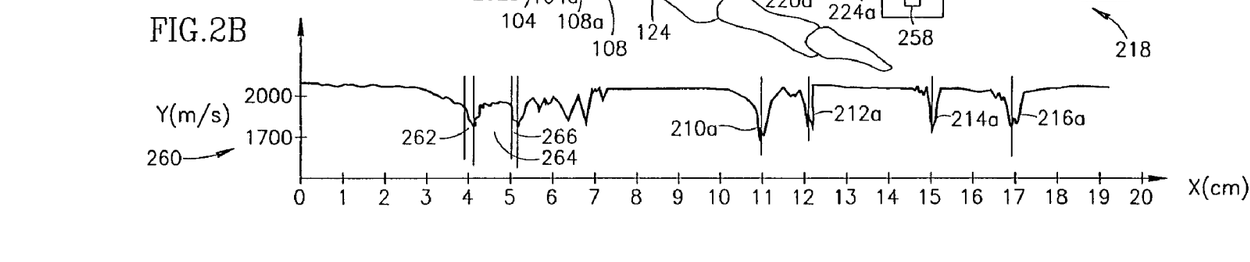
FIG. 2B schematically illustrates a typical graph of ultrasound measurements associated with a path along the bones of FIG. 2A, in accordance with an embodiment of the present invention.

In an exemplary embodiment, ultrasound transmitter 256 and ultrasound receiver 258 are moved along an axis 270. The transducers 256 and 258 are moved in position so that the signal between them passes from the dorsal to ventral surfaces of portions of radius 232, Scaphoid 104, Trapezoid 110, and through a second ray 218 of digit structures 254. FIG. 2B shows an exemplary graph 260 of such ultrasound measurements taken along axis 270. Where the y axis represents the speed of sound and the x axis represents the distance along ray 218 in centimeters.

As ultrasound transducers 256 and 258 pass end of radius 232, the velocity of the acoustic signal, shown in graph portion 262, decreases. As transducers 256 and 258 pass epiphysis 232b, the acoustic velocity increases, as shown in a graph section 264, reflecting the presence of increased ossification within the cartilage. However, as the ossification is not complete, signal 264 does not reflect as high a velocity as prior to signal area 262.

As transducers 256 and 258 pass Scaphoid 104 and Trapezoid 110 along axis 270, a graph area 266 demonstrates a decrease in velocity, reflecting a decrease in ossification in base of Scaphoid 104. Transducers 256 and 258 pass through second ray 218 of digit structures 254, passing a metacarpal 220. As they pass a growth plate 210, there is a corresponding decrease in velocity indicated by a graph region 210a. Transducers 256 and 258 pass a proximal phalanx 222, showing an increased velocity. As they pass a growth plate 212, there is a corresponding decrease in velocity indicated by a graph region 212a. Transducers 256 and 258 pass a middle phalanx 224 with an increase in velocity due to ossification. As they pass a growth plate 214, there is a corresponding decrease in velocity indicated by a graph region 214a. Transducers 256 and 258 pass a distal phalanx 226 with an increase in acoustic velocity. As they pass a growth plate 216, there is a corresponding slow down in acoustic signal indicated by a graph region 216a.

Reduced velocity corresponding to the growth plate position will change until fusion when the growth plate becomes ossified. Typically, the length and shape of the bones will continue to remodel and grow in size until fusion is completed.

In an exemplary embodiment of the invention, the bone age is estimated by comparing the profile of velocity changes along multiple ossifying structures, such as those values contained in graph 260 to a database of standardized profiles. Alternatively or additionally, the bone age is estimated by comparing the velocity at one or more particular anatomical points (e.g., metacarpal 220) to a database of standardized velocities. Optionally, final bone age is an average of a plurality of such bone ages. Alternatively, the bone age is based on an averaging of the velocity at the plurality of points. Additionally or alternatively, the bone age is based on a ratio between average acoustic velocity of a bone, such as metacarpal 220, and a second bone, such as proximal phalanx 222.

In another example, the average acoustic velocity across the width of a bone, such as metacarpal 220, and the acoustic velocity through the length of the same bone 220, are divided to provide a measure of bone age. To provide a measure along the bone length, for example, the finger is bent and measurements are taken along the length of the proximal, middle and distal phalanges either separately or through two or more at along the same axis.

In an exemplary embodiment a database is constructed of bone measurements. The database is used to analyze acoustic signals. Extraction of information from the database can be, for example, via matching received signals to similar signal and values contained in the database, or by interpolation.

In an exemplary embodiment, the information extracted from the database is used as an aid in diagnosis, e.g. estimating a bone age or a disease state. Additionally or alternatively, the extracted information is used for adult height prediction, e.g. final stature. In an exemplary embodiment, height prediction can be made utilizing any of the known formulae and tables stated above. Such a derivation can be arrived at, for instance, by substituting the ultrasound bone age obtained by quantitative ultrasound in place of the bone age obtained by an X-ray film.

In an exemplary embodiment, the database associates one of more of the following items of information with acoustic velocity or acoustic signal parameters: sex, ethnic group, geographic location, nutrition, genetic inheritance. In an exemplary embodiment, the database is created by acquiring acoustic signal measurement in a plurality of subjects, in a plurality of bones, at a plurality of growth stages, and in a plurality of populations. Optionally, the bone age is estimated by comparing acoustic signals to known bone age measurement systems such as those based on X-ray, CT, MRI and Nuclear Medicine. Alternatively to creating a database, the measurements may be used to train a neural network.

In an exemplary embodiment, the database is used as an aid in medical diagnosis and for monitoring. For instance, in conjunction with repeated bone age measurements the database monitors growth hormone therapy that is often administered to children who have short stature. Alternatively, the database can be used to diagnose such conditions as precocious puberty or delayed puberty so that appropriate hormone therapy can be administered. In an exemplary embodiment, multiple measurements of a single subject are stored in a personal database. Such a personal database may be used, for example, for tracking changes in bone age over time or in diagnosing bone-age related disorders. Such disorders, for instance, can be related to malnutrition syndromes such as rickets and kwashiorkor. Additionally or alternatively, such a personal database may be used in tracking treatment of metabolic disease states such as diabetes. Additionally or alternatively, such a personal database may be used in diagnosis and/or treatment of endocrine-related growth disorders such as primary hyperparathyroidism or pituitary dwarfism.

Alternatively or additionally, the measurement or measurements may be compared to data in a data-base that compares such measurements with one or more of adult bone length, density, thickness and resilience to predict one or more of adult bone length, density, thickness and resilience.

In an exemplary embodiment, transducer frequency is between 300 kHz to 5 MHz. When the structures being measured are more superficial, as in digit structures 254, a frequency closer to 5 MHz can be used as there is less attenuation of the ultrasound signal and a higher signal to noise ratio that improves the quality of signal. Along the mid shaft of the femur, for instance, a frequency near 200 kHz is used, as a higher frequency may be attenuated excessively while going through several centimeters of tissue.

When greater clarity of microstructure is desired, such as in spatial radial measurement of the bone growth center, a higher ultrasound frequency, such as 10 MHz or even 50 MHz or higher may be used. With alternative transducer design, higher or lower frequencies can be utilized.

In an exemplary embodiment, an existing osteoporosis measurement device, such as the DBM Sonic 1200 ultrasound system by IGEA of Carpi (Mo), Italy, is modified to provide a bone age estimate. In an exemplary embodiment, a database is reprogrammed with a table that associates acoustic velocities with bone ages, rather than with states of osteoporosis. Additionally or alternatively, a gantry 274 and ultrasound transducers 256 and 258 are electronically controlled by computer system 142. In an exemplary embodiment, parameters such as transducer positional changes and acoustic signal, are automatically effected by the computer system's analysis of the acoustic signal against an ultrasound bone age database for the purpose of obtaining optimal bone age data from ray 218.

Growth plates, such as growth plate 212, exhibit patterns of interdigitation with adjacent areas of bone 222 and this interdigitation may exhibit changes that can be used to forecast stature, metabolic bone health and age. In an exemplary embodiment, multiple measurements with transducers 256 and 258 are taken radially while rotating the transducers around a growth plate 212 of bone 222 to provide a spatial map of growth plate 222 interdigitation.

Additionally or alternatively, acoustic signals of interdigitation can be used for detecting signs of disease associated with growing bones. Osteogenic sarcoma, for example, is a cancer that often begins from a growth plate such as in the knee. Ossification patterns in a growth plate affected by osteogenic sarcoma generally exhibit differences as compared to a normal growth plate, which differences can support early detection using ultrasound. Optionally, ultrasonic measurements are used for screening for various conditions.

Acoustic signals from the radial movement—a movement along line 270—of transducers 256 and 258 are entered into computing means 142 and can be viewed on visual display 140, for instance as a graph 260. Additionally or alternatively, display 140 provides an image of the bone and accompanying data, or a database of information based on sex, race and/or other factors. Such information can be printed on printer 144.

Figure 3A:
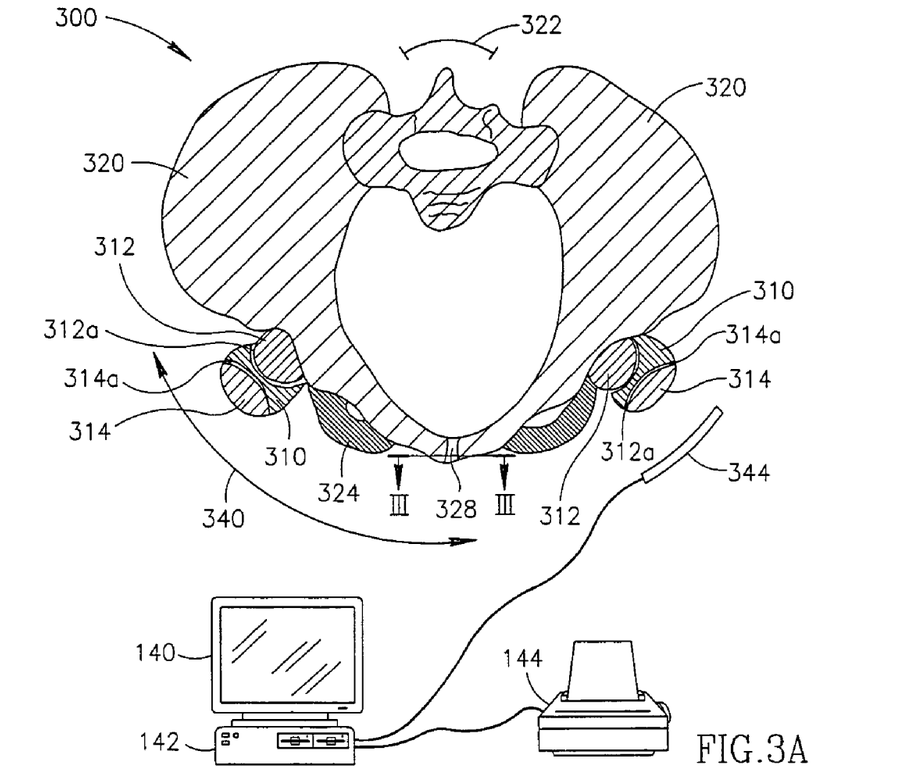
FIG. 3A schematically illustrates ultrasound measurements of ossifying femora and pelvis of a male, age 14, shown in a radiographic representation in accordance with an embodiment of the present invention.

FIG. 3A Illustrates ultrasound measurements of femora 310 and a pelvis 300 of a male age 14 using the echo method of transducer measurement in accordance with an embodiment of the present invention. Shown in FIG. 3A are an illium 320, a sacrum 322 and an ishium 324 that are shaded to demonstrate ossification. An ultrasound transducer 344 contains one or more receivers and transmitters of acoustic signals arranged, for example, in a grid pattern. Probe 344 is shown sending and receiving acoustic signals to femur 310 to scan a femoral head 312 and a femoral trochanter 314. Femoral head 312 develops a secondary ossification center 312a at six months after birth and fuses with femur 310 at age 14 in females and 17 in males. In backscatter attenuation measurements, ultrasound signal reflecting off a bone produces backscatter, picked up by the receiver in the echo method. The backscatter attenuates according to the density of material from which it is received, so that the bone content of a particular tissue is assessed. Hence, transducer 344 may be used to measure backscatter attenuation to determine the ossification level of the location of growth plates in femora 310. For example, greater trochanter 314 develops a secondary ossification center 314a in the fourth year and fuses with femora 310 at age 14 in females and 17 in males. Ultrasound probe 344 measures bone age based on the backscatter attenuation of an acoustic signal in one or more of these structures to determine age.

Additionally or alternatively, probe 344 is rotated along an arc 340 to provide an ossification ratio of femur 310 and pelvis 300 using backscatter attenuation, for instance, as a measure of bone age. Optionally such measurement includes acoustic signal information of a pubic symphysis 328. Additionally or alternatively, probe 344, containing both a receiver and transmitter, is rotated fully around pelvis 300 using the echo method of measurement, obtaining information from backscatter attenuation of ultrasound signal.

Additionally or alternatively, a receiver probe is placed along line III, on one side of pubic symphysis 328 and a transmitter probe is placed at the opposite end of line III so that Broadband ultrasound attenuation can be measured from the pubic symphysis, 328. As in other measurements, a ratio between broadband ultrasound attenuation velocities of these structures, using two or more broadband ultrasound attenuation measurements and/or averages of broadband ultrasound attenuation within each structure can be used to measure bone age.

In an exemplary embodiment, probe 344 indicates and/or tracks a disease state such as slipped capitus femoris, where femoral head 312 is displaced on femur 310. Additionally or alternatively, ultrasound probe 344 is positioned over pubic symphysis 328 to give acoustic velocity information. To determine SOS, two or more transducers should be contained in the probe or two or more separate transducers should be used.

Figure 3B:
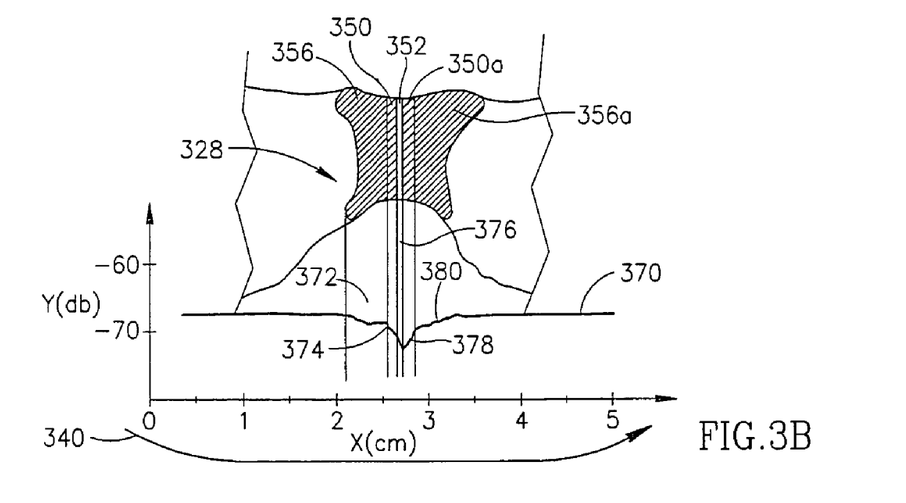
FIG. 3B schematically illustrates a pubic symphysis, shown in cross-section and a typical graph of its ultrasound measurement in accordance with an embodiment of the present invention.

FIG. 3B illustrates a cross-sectional diagram of a pubic symphysis 328 along line III-III in a mature male and an associated graph 370 of acoustic backscatter attenuation. Pubic symphysis 328 is made up of an interpubic disc 352 that is fibrocartilaginous hyaline cartilage. One either side is hyaline cartilage 350 and 350a and a portion of a pubic tubercle 356 and 356a. Pubic tubercle 356 is ossified at age 14.

In graph 370, as the acoustic signal measures pubic tubercle 356, the acoustic backscatter is high due to the ossification content of the bone, corresponding to a region 372 of graph 370. At hyaline cartilage 350, the acoustic backscatter decreases as seen in a region 374 of graph 370, due to the lack of ossification of this structure. At interpubic disc 352 the signal backscatter decreases even further, as seen in a region 376 of graph 370, as this structure is fibrocartilaginous, with less dense fibers interspersed in the cartilage.

At hyaline cartilage 350a the signal backscatter increases representing the greater density of hyaline cartilage as shown in an area 378 in graph 370. At pubic tubercle 356a, the signal backscatter increases even further representing the greater density of bone as represented by an area 380 of graph 370.

According to T. W. Todd, in "Age changes in the pubic bones," *Am. J. Phys. Anthropology,* 3:285-334 and T. W. McKern and T. D. Stewart, "Skeletal age changes in young American males" Tech Rep. EP 45. Environmental Protection Research Div. Natick, Mass., changes within the pubic symphysis, such as changes in the bony surfaces, occur from the late teens to the fifties and beyond. Similarly, skeletal age is measured by the appearance and changes in the cranial sutures above 25 years of age. (T. W. Todd and D. W. Lyon, "Endocranial suture closure, its progress and age relationship. *Am. J. Phys. Anthropol.* 7:325-384). Thus, using acoustic signals in one or more structures that exhibit changes after bone growth has ceased in the long bones of the body, bone age can continue to be measured. Such measurements can also be used to indication the presence of a disease such as acromegaly, a diagnosis that can be confirmed by measuring the amount of somatotropin hormone production in the blood.

While the invention has been described with respect to limited number of embodiments, it will be appreciated that many variations, modifications and other applications of the invention may be made. Also, combination of elements from variations may be combined and single elements may be used. Any and all such variations and modifications, as well as others that may become apparent to those skilled in the art are intended to be included within the scope of the invention, as defined by the appended claims.

The terms "include", "comprise" and "have" and their conjugates as used herein mean "including but not necessarily limited to."

It will be appreciated by a person skilled in the art that the present invention is not limited by what has thus far been described. Rather, the scope of the present invention is limited only by the following claims.

The invention claimed is:

1. A method for measuring bone age comprising:
    (a) providing an apparatus for estimating bone age by at least one acoustic signal in an ossification-actuated skeletal structure, comprising:
        (I) an acoustic transmitter and an acoustic receiver positioned facing each other so that said structure is positioned between them; said structure comprises at least two bones; said transmitter is adapted for transmitting said at least one signal to cross said structure transversely; said receiver is adapted for receiving said at least one signal transmitted by said transmitter;
        (II) an electronic moveable gantry for adjusting the position of said acoustic transmitter and said acoustic receiver in relation to said structure;
        (III) a computer system enabled to estimate said bone age responsive to said received signal by at least one bone age calculation formula,
    (b) transmitting said at least one signal into said structure by said transmitter;
    (c) receiving said transmitted at least one signal by said receiver;

(d) analyzing said at least one signal and determining at least one effect of said structure on said at least one signal; and (e) estimating the age of said structure by using said determined effect and said at least one formula.

2. The method according to claim 1 wherein said structure comprises one or more areas undergoing ossification.

3. The method according to claim 1 wherein said estimating of said bone age is in terms of years and months.

4. The method according to claim 1 wherein said structure comprises one or more regions of cartilage.

5. The method according to claim 1 wherein said structure comprises one or more regions of non-cartilage soft tissue.

6. The method according to claim 5 wherein said structure comprises one or more regions of fibrocartilage.

7. The method according to claim 1 wherein said structure comprises a region with one or more primary ossification centers.

8. The method according to claim 7 wherein said structure comprises one or more of: the bones of the wrist.

9. The method of claim 7 wherein said structure comprises one or more epiphyseal growth plates.

10. The method according to claim 1 wherein said structure comprises a region with one or more secondary ossification centers.

11. The method of claim 10 wherein said structure comprises a region of one or more of: an ulna, a radius a femur.

12. The method of claim 11 wherein said ulna is the distal end of the ulna; wherein said radius is the distal end of the radius.

13. The method according to claim 1 wherein said step of transmitting further comprises transmitting at least two signals crossing different paths in said structure and said step of receiving comprises receiving said at least two signals.

14. The method according to claim 1 wherein said step of determining at least one effect of said structure on said at least one signal is selected from a group consisting of: speed of sound, broadband ultrasound attenuation, dispersion of ultrasound.

15. The method according to claim 14 wherein said step of determining at least one effect is performed, at least in part, in the frequency domain.

16. The method according to claim 14 wherein said step of determining at least one effect is performed, at least in part, in the time domain.

17. The method according to claim 14 wherein said step of determining at least one effect is responsive to attenuation of said signal in said structure.

18. The method according to claim 14 wherein said step of determining at least one effect further comprises a step of comparing said determined effect to a database having correlation with various other relevant effects determined from one or more of the following imaging techniques for bone age estimation: conventional radiographs, CT images, MRI images and Nuclear Medicine scans.

19. The method according to claim 18 comparing said determined effect is further comprising a step of predicting one or more of adult bone length, density, thickness and, resilience and adult stature.

20. The method according to claim 18 wherein comparing said determined effect is for indicating one or more of: a bone-growth related disorder, a growth plate disorder and a growth related disorder.

21. The method according to claim 18 wherein comparing said determined effect is for tracking the progress of a bone-growth related disorder.

22. The method according to claim 18 wherein said comparing said determined effect is for tracking hormone therapy in a growth stature disorder.

23. The method according to claim 18 wherein comparing said determined effect is for indicating one or more of: growth-plate related disease states, including osteogenic sarcoma, slipped growth plate, premature arrest of growth plate growth and inflammation of growth plate.

24. The method according to claim 1 wherein said step of estimating the age of said structure is used to estimate adult stature.

25. The method according to claim 1 wherein said transmitter is a scanning acoustic signal transmitter.

26. The method according to claim 1 wherein said transmitter is a multi-beam acoustic signal transmitter.

27. The method according to claim 1 wherein said step of estimating the age of said structure is correlated with a known bone age measurement system.

28. The method according to claim 1 wherein said step of estimating the age of said structure is responsive to a formula providing a correlation with a known bone age measurement system.

29. The method according to claim 28 wherein said formula is responsive to at least one of: speed of sound, broadband ultrasound attenuation, scattering and dispersion of acoustic signal through or from said structure.

30. The method according to claim 28 wherein an estimate of bone age is responsive to time of flight of an acoustic signal between two transducers, with said structure being situated intermediate to said transducers.

31. The method according to claim 1 further comprises a step of transferring said age and said at least one signal into a database of bone age measurements.

32. The method according to claim 31 wherein said database is arranged according to one or more of: sex, ethnic group, geographic location, nutrition and general inheritance.

33. The method according to claim 31 wherein said database includes two or more measurements of one or more of said structure.

34. The method according to claim 31 wherein said database includes one or more measurements of two or more growth stages from said structure.

35. The method according to claim 31 wherein said database includes one or more measurements of said structure in two or more populations.

36. The method according to claim 31 further comprising a step of tracking one or more growth-related disorders, including precocious puberty, delayed puberty, rickets, kwashiorkor, hypoparathyroidism, pituitary dwarfism and diabetes.

37. An apparatus for estimating bone age by at least one acoustic signal in an ossification-actuated skeletal structure, comprising (a) acoustic transmitter and an acoustic receiver positioned facing each other so that said structure is positioned between them; said structure comprises at least two bones; said transmitter is adapted for transmitting said signal to cross said structure transversely; said receiver is adapted for receiving said at least one signal transmitted by said transmitter;

(b) an electronic moveable gantry adjusts the position of said acoustic transmitter and said acoustic receiver in relation to said structure;

(c) a computer system enabled to estimate said bone age responsive to said received signal by at least one bone age formula.

38. The apparatus of claim 37 wherein said computer system controls said transmitter to provide said signal appropriate for said structure.

39. The apparatus of claim 37 wherein said computer system estimates said bone age responsive to one or more of: broadband ultrasound attenuation, acoustic backscatter, dispersion of acoustic signal and speed of sound in said structure.

40. The apparatus of claim 37 wherein said computer system uses an imager to control the position of said acoustic signal receiver and said acoustic signal transmitter.

41. The apparatus of claim 37 said computer system contains a visual display to provide information on said bone age.

42. The apparatus of claim 41 wherein said visual display comprises a graph.

43. The apparatus of claim 37 wherein said computer system is comprised in a computer network.

44. The apparatus of claim 37 wherein said computer system comprises a neural network.

45. The apparatus of claim 37 wherein said computer system compares said signal to a database containing information of one or more acoustic signals from one or more other ossification-actuated skeletal structures to provide an estimate of bone age.

* * * * *